(12) United States Patent
Wu et al.

(10) Patent No.: US 9,289,614 B2
(45) Date of Patent: Mar. 22, 2016

(54) SYSTEM AND METHOD FOR COMMUNICATING WITH AN IMPLANTABLE MEDICAL DEVICE

(71) Applicant: Pacesetter, Inc., Sunnyvale, CA (US)

(72) Inventors: Yongjian Wu, Saratoga, CA (US); Jun Yang, Valencia, CA (US); Chao-Wen Young, Cupertino, CA (US); Reza Shahandeh, Thousand Oaks, CA (US); Thanh Tieu, Simi Valley, CA (US); Min Yang, Los Altos, CA (US); Jorge N. Amely-Velez, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 127 days.

(21) Appl. No.: 14/218,590

(22) Filed: Mar. 18, 2014

(65) Prior Publication Data

US 2015/0265843 A1    Sep. 24, 2015

(51) Int. Cl.
*A61N 1/372* (2006.01)
*A61N 1/05* (2006.01)
*A61N 1/36* (2006.01)

(52) U.S. Cl.
CPC ............ *A61N 1/37252* (2013.01); *A61N 1/056* (2013.01); *A61N 1/3605* (2013.01); *A61N 1/3727* (2013.01); *A61N 1/37276* (2013.01)

(58) Field of Classification Search
CPC . A61N 1/37252; A61N 1/3605; A61N 1/056; A61N 1/3727; A61N 1/37276
See application file for complete search history.

(56) References Cited

U.S. PATENT DOCUMENTS

| 2010/0036462 | A1* | 2/2010 | Ramakrishnan | A61N 1/08 607/60 |
| 2010/0312188 | A1* | 12/2010 | Robertson | A61B 5/0006 604/156 |
| 2011/0202103 | A1* | 8/2011 | Wikman | A61N 1/37276 607/25 |

* cited by examiner

*Primary Examiner* — Rex R Holmes
(74) *Attorney, Agent, or Firm* — Theresa A. Raymer

(57) ABSTRACT

A method for operating an implantable medical device (IMD) implanted within a patient may include scanning for a wakeup request signal from an external programmer over a first frequency band at a first power level, switching to communication over a second frequency band at a second power level after the IMD detects the wakeup request signal, wherein the switching operation initiates an initial data exchange session during a common connected time period between the IMD and the external programmer, and cycling between the first and second power levels during the common connected time period based on whether data is being exchanged between the external programmer and the IMD.

22 Claims, 10 Drawing Sheets

SYSTEM AND METHOD FOR COMMUNICATING WITH AN IMPLANTABLE MEDICAL DEVICE

BACKGROUND OF THE DISCLOSURE

Embodiments of the present disclosure generally relate to implantable medical devices, and more particularly to implantable medical devices that communicate with an external device through radio frequency (RF) signals.

Numerous medical devices exist today, including but not limited to electrocardiographs ("ECGs"), electroencephalographs ("EEGs"), squid magnetometers, implantable pacemakers, implantable cardioverter-defibrillators ("ICDs"), neurostimulators, electrophysiology ("EP") mapping and radio frequency ("RF") ablation systems, and the like. Implantable medical devices (hereafter generally "implantable medical devices" or "IMDs") are configured to be implanted within patient anatomy and commonly employ one or more leads with electrodes that either receive or deliver voltage, current or other electromagnetic pulses (generally "energy") from or to an organ or tissue for diagnostic or therapeutic purposes.

Various IMDs are monitored by a programmer or base station that is remotely located from the IMDs. For example, a patient may have an IMD that communicates with a base station within the patient's home. The base station may be located by a patient's bedside. The base station receives data from the IMD regarding the patient's physiological state and/or the operation state of the IMD. Based on the received data, the base station may convey the data to a remote server of a medical care network, or adjust operating parameters for the IMD. For example, the base station may adjust operating parameters of the IMD, such as when a patient experiences changes in arrhythmia, pacing, ST shift, various types of ischemia, base rate, and the like.

Many IMDs include an RF capability to communicate with the programmer. Data may be received from the base station when transmitted over varies frequency bands, such as at a 402-405 MHz frequency range, which represents the Medical Implant Communication Service (MICS) band. The MICS band enables a short-range, wireless link to be maintained between low-power implanted IMDs and an external programmer or base station.

An RF chip within a typical IMD periodically scans select frequency bands, such as the 2.45 GHz band, over the life of the IMD. The 2.45 GHz band is an unlicensed, microwave band. The IMD uses information received over the 2.45 GHz band to determine if the programmer is seeking to communicate with the IMD over another band (for example, the MICS band), which is used to receive and transmit data to and from the IMD. If the RF chip operating at a 2.45 GHz band detects that the programmer desires to communicate over the MICS band, the IMD then switches over to the MICS band. Bidirectional communication over the MICS band consumes substantially more power than the 2.45 GHz band. As such, through the use of the 2.45 GHz band, which is used to detect whether the programmer is attempting to communicate with the IMD, the IMD conserves energy. In general, the MICS band (for example, the 402-405 MHz band) affords a longer range and more robust connection than the 2.45 GHz band. However, as compared to the MICS band, the 2.45 GHz band draws less power from the IMD when scanning for connection requests and during a communications session.

The MICS band has been used with IMDs such as pacemakers. In general, communication between a pacemaker and a base station may occur less than five times per day, with each communication session being relatively short, such as less than two or three seconds.

In contrast, certain IMDs, such as neurostimulators-communicate with a base station with increased frequency, as compared to pacemakers, and for longer periods. Accordingly, neurostimulators typically communicate with base stations through inductive communication, as communication using the MICS band typically draws excessive power from the neurostimulators. In an inductive communication system, communication may occur between the IMD, such as a neurostimulator, and a telemetry wand that is operatively connected to the base station. Typically, the wand of the base station or programmer is placed in close proximity to the IMD in order to establish a communication link.

Accordingly, use of the MICS band to facilitate communication between a neurostimulator and a base station has generally not been considered because the neurostimulator would need to use an amount of energy to communicate using the MICS band that would reduce the longevity of the neurostimulator.

SUMMARY

Embodiments of the present disclosure provide systems and methods for communicating between an IMD, such as a neurostimulator, and a base station using the MICS band, for example.

Certain embodiments of the present disclosure provide a method for operating an implantable medical device (IMD) implanted within a patient. The method may include scanning for a wakeup request signal from an external programmer over a first frequency band at a first power level, and switching to communication over a second frequency band at a second power level after the IMD detects the wakeup request signal. The switching operation initiates a common connected time period that includes one or more data exchange sessions between the IMD and the external programmer. The method may also include cycling between the first and second power levels during the common connected time period based on whether data is being exchanged between the external programmer and the IMD.

In at least one embodiment, the cycling operation may include operating at the first power level during the common connected time period when no data is being exchanged between the external programmer and the IMD, and operating at the second power level during the data exchange session when data is being exchanged between the external programmer and the IMD. The cycling operation may include communicating with the external programmer at the second frequency band at the second power level during the data exchange session. In at least one embodiment, the second power level may exceed the first power level. In at least one embodiment, the first frequency band may be a 2.45 GHz band, while the second frequency band may be a Medical Implant Communication Service (MICS) band.

The method may also include determining that no data is being exchanged during the common connected time period, switching to the first power level during the common connected time period after the determining operation, activating a re-wakeup timer after the determining operation during the common connected time period, and switching to the second power level at the end of the re-wakeup timer to determine whether the external programmer is attempting to exchange data with the IMD.

The method may also include receiving a data cessation signal from the external programmer, and switching back to the scanning operation upon the receiving operation.

Certain embodiments of the present disclosure provide a system for conserving power during a common connected time period that may include one or more data exchange sessions. The system may include an external programmer configured to transmit a wakeup request signal, and an implantable medical device (IMD) configured to be implanted within a patient and communicate with the external programmer. The IMD scans for the wakeup request signal from the external programmer over a first frequency band at a first power level, and switches to a second frequency band at a second power level after the IMD detects the wakeup request signal to initiate a data exchange session. The IMD cycles between the first and second power levels during the common connected time period based on whether data is being exchanged between the external programmer and the IMD.

The IMD may be configured to operate at the first power level during the common connected time period when no data is being exchanged between the external programmer and the IMD, and to operate at the second power level during a data exchange session when data is being exchanged between the external programmer and the IMD.

The IMD may include a re-wakeup timer that is activated after one or both of the external programmer and the IMD determine that no data is being exchanged during the common connected time period. The IMD switches to the second power level at the end of the re-wakeup timer to determine whether the external programmer is attempting to exchange data with the IMD.

In at least one embodiment, the IMD may include a wakeup detection module configured to scan for the wakeup request signal from the external programmer over the first frequency band at the first power level. One or both of the external programmer and the IMD may include a data exchange detection module configured to detect whether data is being exchanged between the external programmer and the IMD. One or both of the external programmer and the IMD may include a power setting adjustment module configured to cycle the IMD between the first and second power levels during the common connected time period based on whether data is being exchanged between the external programmer and the IMD.

In at least one embodiment, after receiving a data cessation signal from the external programmer, the IMD is configured to switch back to scanning for the wakeup request signal from the external programmer over the first frequency band at the first power level.

DETAILED DESCRIPTION

Figure 1:
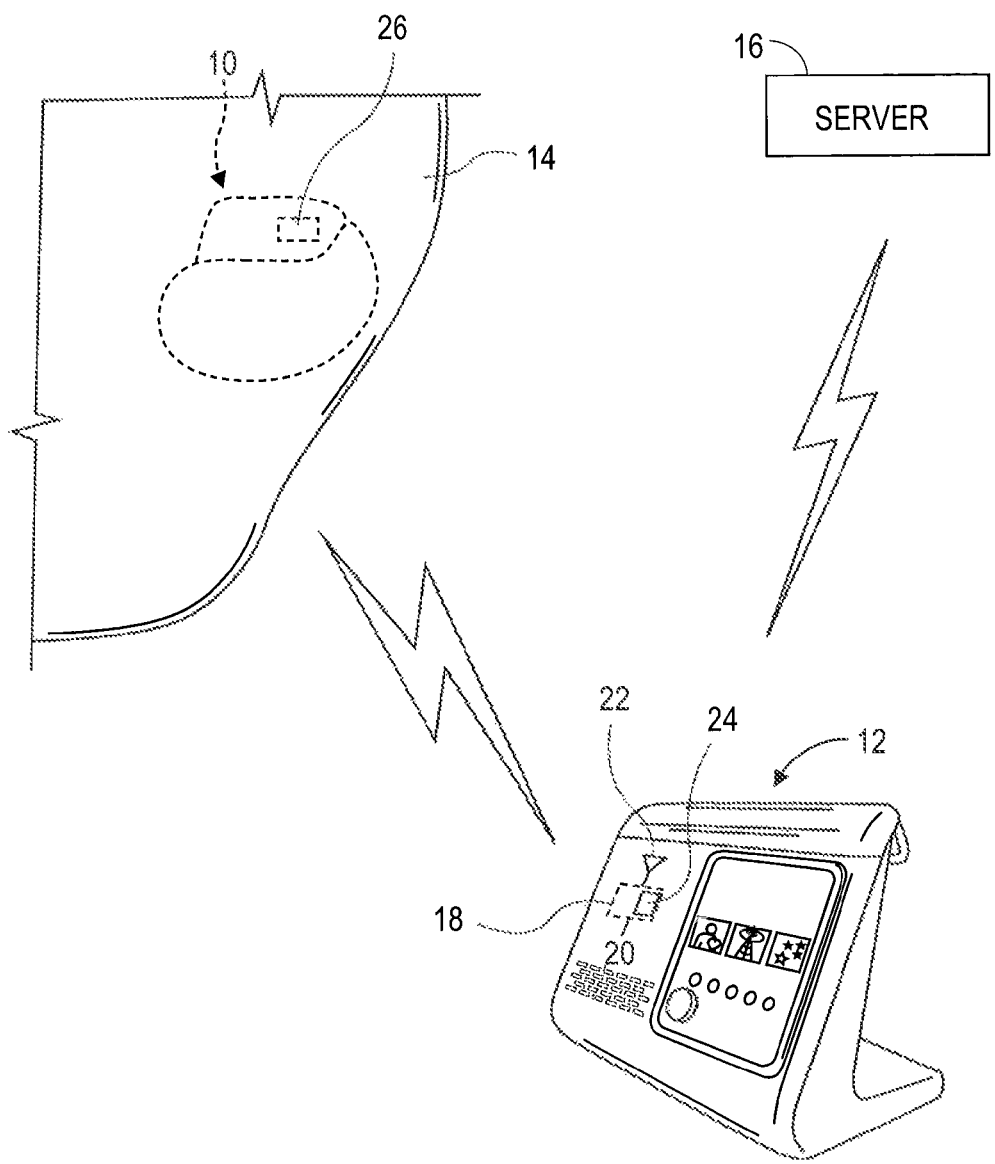
FIG. 1 illustrates a simplified view of an IMD and an external programmer, according to an embodiment of the present disclosure.

FIG. 1 illustrates a simplified view of an IMD 10 and an external programmer 12, such as a base station or patient care system (PCS), according to an embodiment of the present disclosure. The IMD 10 may be implanted within a patient 14. The remotely-located programmer 12 monitors the IMD 10. The programmer 12 may be located within a medical care facility, such as a hospital or clinic, or within a home of the patient 14, in his/her vehicle, at his/her office, and the like. When the programmer 12 is located within the patient's home, the programmer 12 may be proximate to a bed of the patient 14. The programmer 12 functions as a base station that wirelessly communicates with the IMD 10. The programmer 12 may also communicate with a remote server 16 within a patient care network, such as over a phone link, cellular link, Internet connection, local area network, wide area network and the like.

The programmer 12 performs various functions, such as operating as an intermediate relay device to collect and store patient physiologic data, IMD operational status data, and the like. The physiologic data may be electrical data related to a physiologic condition. The programmer 12 may then transmit the physiologic data, IMD operational status data and other data to the remote server 16 of the patient care network. Physicians and other personnel can monitor the patient and collect data over the patient care network. Also, the programmer 12 may receive updates, upgrades, and other IMD control-related information from the patient care network and relay the IMD control-related information to the IMD 10.

The IMD 10 may be one of various types of implantable devices, such as, for example, an implantable pacemaker, implantable cardioverter-defibrillator ("ICD"), defibrillator, cardiac rhythm management ("CRM") device, neurostimulator, or the like.

The programmer 12 may include a standalone antenna assembly. The programmer 12 may represent the Merlin® home patient care system offered by St. Jude Medical. The programmer 12 may include an RF telemetry subsystem 18 that communicates with the IMD 10 and/or the server 16. The telemetry subsystem 18 may include an RF telemetry circuit 20 operatively connected to one or more MICS antennas 22. The telemetry circuit 20 may also include or be operatively connected to a controller, processing unit or circuit 24. Alternatively, the programmer 12 may represent a handheld portable tablet-type programmer device used by physicians and others to communicate with, collect data from, program, and reprogram the IMD 10. Also, alternatively, the programmer 12 may be a cell phone, personal computer, or laptop computer.

In operation, an RF chip 26 within the IMD 10 periodically scans a first frequency band, such as a low-power, high frequency band or channel. For example, the first frequency band may be an unlicensed, microwave band, such as the 2.45 GHz band. The IMD 10 uses information received over the first frequency band to determine if the programmer 12 is seeking to communicate with the IMD 10 over a second frequency band or channel, such as a higher power, lower frequency band, such as the MICS band, which is used to receive and transmit data to and from the IMD 10. If the RF chip within the IMD 10 operating at the first frequency band detects that the programmer 12 desires to communicate over the second frequency band, the IMD 10 may switch over to the second frequency band.

A wand (not shown) may also be used to establish a communication link between the IMD 10 and the programmer 12. The wand may include an RF transmitter that transmits an RF wake-up call to the IMD 10 when in close proximity to the IMD 10. For example, the wand may be positioned within 0-1 meters from the IMD 10 in order to wake the IMD 10 up so that a communication link between the IMD 10 and the programmer 12 may be established. Alternatively, the wand may be able to wake the IMD 10 up at ranges longer than 1 meter. Once the wand transmits an RF wake signal to the IMD 10, the IMD 10 may then switch from the first frequency band to the second frequency band in order to communicate with the programmer 12. Also, the wand may be configured to be removably connected to a handheld device, such as an iPhone, iPad, Kindle, and/or the like.

Figure 2:
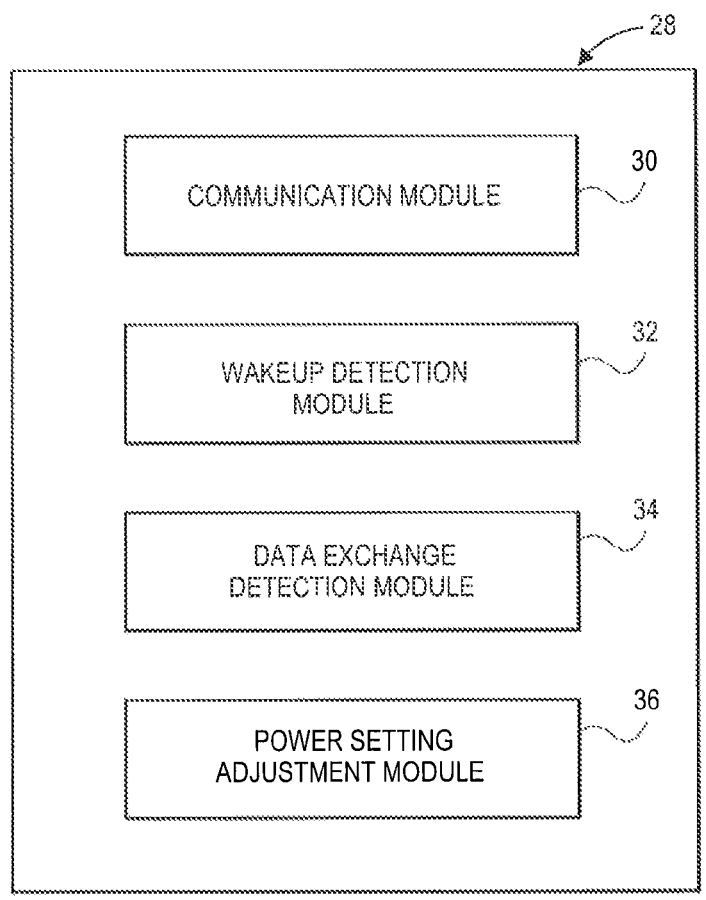
FIG. 2 illustrates a functional block diagram of a power regulator of an IMD, according to an embodiment of the present disclosure.

FIG. 2 illustrates a functional block diagram of a power regulator 28 of an IMD, according to an embodiment of the present disclosure. The power regulator 28 may be or include a control unit, circuitry, processor, or the like housed within an IMD. For example, the power regulator 28 may be part of the RF chip 26 (shown in FIG. 1) of the IMD 10.

The power regulator 28 may include a communication module 30 configured to communicate with an external programmer, a wakeup detection module 32 configured to determine if the external programmer has transmitted a wakeup request signal to initiate a communication session or common connected time period, a data exchange module 34 configured to exchange data between the IMD and the programmer, and a power setting adjustment module 36 configured to adjust power level settings of the IMD depending on whether data is being exchanged between the IMD and the programmer. For example, the power setting adjustment module 36 may be configured to switch between a first power level (such as a low power level setting) associate with communication over the first frequency band and a second power level (such as a high or elevated power level setting) associated with communication over the second frequency band.

The term data exchange includes data transmitted from one of the IMD or the external programmer/base station to the other of the IMD or the external programmer/base station. The term data exchange also includes the IMD transmitting data to the external programmer/base station while the external programmer/base station transmits data to the IMD.

In operation, the communication module 30 may be operatively connected to antennas an antenna configured to communicate with the programmer. The wakeup detection module 32 periodically scans a first frequency band to determine if the programmer has transmitted a wakeup request signal over the first frequency band. If the wakeup detection module 32 does not detect a wakeup request signal transmitted by the programmer, the wakeup detection module 32 continues to periodically scan the first frequency band for a wakeup request signal. If, however, the wakeup detection module 32 does detect a wakeup request signal on the first frequency band, the wakeup detection module 32 switches to the second frequency band that is configured to support data exchange between the IMD and the programmer. As noted, the IMD may switch to a high power level setting in order to communicate over the second frequency band.

The data exchange module 34 allows for data to be exchanged between the IMD and the programmer. For example, the data exchange module 34 communicates with the programmer through the communication module 30 to determine if data is being exchanged therebetween. Optionally, the IMD may not include the data exchange module 34. Instead, the external programmer or base station may include the data exchange module 34 and/or transmit a data cessation signal to the IMD in order to inform the IMD that data is no longer being exchanged.

The power setting adjustment module 36 adjusts the power level setting of the IMD during the communication session between the IMD and the programmer based on whether data is being exchanged therebetween, as detected by the data exchange module 34 and/or transmitted by the external programmer or base station. If data is being exchanged between the IMD and the programmer, the power setting adjustment module 36 maintains the IMD in a full power setting in order to enable communication of the data with the external programmer (such as over the second frequency band). If, however, the data exchange detection module 34 determines that no data is being exchanged, the power adjustment setting module 36 switches to a reduced or low power setting during the communication session in order to conserve energy of the IMD. For example, the power adjustment setting module 36 may switch back to a power level that enables communication over the first frequency band. Alternatively, the power adjustment setting module 36 may reduce the power level even lower, such as a low power level that enables a re-wakeup timer to be operated. Also, alternatively, the external programmer may include the power setting adjustment module 36. As such, the external programmer may send signals to the IMD that switch the IMD between low and high power settings, for example.

As noted, the low power setting or sleep mode may be a power level used to communicate (for example, scan or sniff) over a first frequency band or channel, such as the 2.45 GHz band. A high power setting may be a power level used to communicate (for example, exchange data) over a second frequency band or channels, such as the MICS band. Alternatively, the low power setting or sleep mode may be a power level that does not relate to communication over the first frequency band or channel. Instead, the low power setting or sleep mode may be a power setting that allows a reduced set of components to be operated, such as operation of a re-wakeup timer, as described below. Also, alternatively, the high power level may be a power level that does not relate to communication over the second frequency band or channel.

The terms "low" and "high" in relation to the power settings are relative terms. That is, the low power setting is low, lower, or otherwise reduced as compared to the high power setting, which is high, higher, or otherwise elevated as compared to the low power setting. For example, the high power setting may be a standard power setting, while the low power setting is a power setting that is less than the standard power setting. For example, the low power setting may be a setting in which the communication module 30 is deactivated, and only consumes less than 1000 nA of current. The high power setting may be a setting in which the communication module is fully active and exchanges radio information with a programmer every 10 ms, and may consume 3.5-5.5 mA in current.

It is to be understood that the first frequency band or channel may be another band or channel other than the 2.45 GHz band. Similarly, the second frequency band or channel may be another band or channel other than the MICS band. In general, the first frequency band may be a band or channel that an IMD may expend less power communicating on or over, as compared to the second frequency band.

Each module 30, 32, 34, and 36 may include one or more control units, such as processing devices that may include one or more microprocessors, microcontrollers, integrated circuits, memory, such as read-only and/or random access memory, and the like. The modules 30, 32, 34, and 36 may be integrated into a single module, control unit, circuit, or the like, and contained within a single device, such as a single integrated chip, for example. Alternatively, each module 30, 32, 34, and 36, may be its own separate and distinct module, and contained within a respective integrated chip, for example.

One or more of the modules 30, 32, 34, and 36 may include any suitable computer-readable media used for data storage. For example, one or more of the modules 30, 32, 34, and 36 may include computer-readable media. The computer-readable media are configured to store information that may be interpreted by the modules 30, 32, 34, and 36. The information may be data or may take the form of computer-executable instructions, such as software applications, that cause a microprocessor or other such control unit within the modules 30, 32, 34, and 36 to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

Figure 3A:
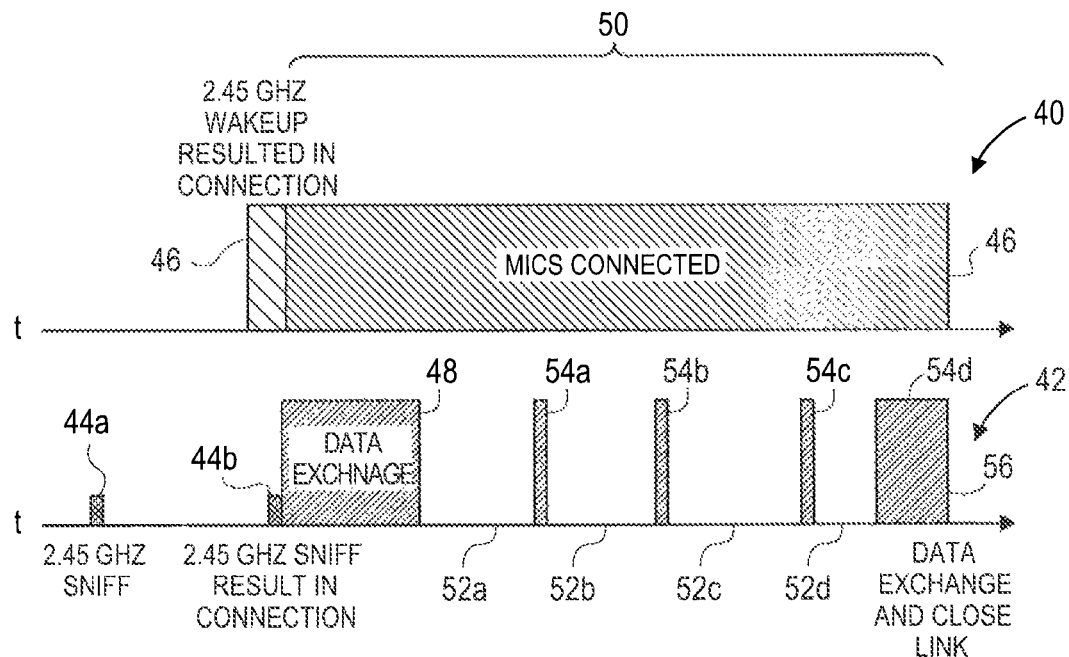
FIG. 3A illustrates a timing diagram of data exchange between a programmer and an IMD, according to an embodiment of the present disclosure.

FIG. 3A illustrates a timing diagram of data exchange between a programmer 40 and an IMD 42, according to an embodiment of the present disclosure. Referring to FIGS. 2 and 3, the IMD 42, such as through an RF chip of the communication module 30, periodically scans a first frequency band, such as a low power, high frequency band, such as the 2.45 GHz band, for example. In general, the IMD 42 scanning or sniffing at the 2.45 GHz band while awaiting a wakeup request signal or request from the programmer consumes a relatively small amount of current, as compared with operation at the MICS band, for example. The wakeup detection module 32 may initiate periodic scans 44a and 44b at regular intervals. For example, the wakeup detection module 32 of the IMD 42 may periodically scan the first frequency band every thirty seconds. Alternatively, the time period between the periodic scans 44a and 44b may be greater or less than thirty seconds.

During the scan 44a of the first frequency band, the programmer 40 is not transmitting a wakeup request signal. Accordingly, the IMD 42, such as through the wakeup detection module 32, does not transition to a data exchange mode with the programmer 40.

During the scan 44b, however, the programmer 40 transmits a wakeup request signal 46, indicating that the programmer 40 is seeking to communicate with the IMD 42 over a second frequency band, such as a higher power, lower frequency band, such as the MICS band, which is used to receive and transmit data to and from the IMD 42. The wakeup detection module 32 detects the wakeup request signal 46 (for example, the scan 44b "handshakes" the wakeup request signal 46), and transitions the IMD 42 to the second frequency band to initiate a data exchange session during a common connected time period, in which data is exchanged between the IMD 42 and the programmer 40 over the second frequency band.

Once the data exchange session is initiated, the programmer 40 establishes a communication link 50 with the IMD 42 over the second frequency band during a common connected time period. During the communication link 50, the programmer 40 may communicate over the communication link 50 at full power or the high power setting (such as a power level that enables communication over the MICS band).

In order to conserve energy, the IMD 42 cycles between full power and low power settings, depending on whether the programmer 40 is requesting data from, or transmitting data to, the IMD 42. For example, once the data exchange session is initiated, the data exchange detection module 34 of the IMD 32 may detect that the programmer 40 is requesting that data be exchanged with the IMD 42. Therefore, the IMD 42 communicates at a high power setting with the programmer 40 during the data exchange 48, until the data exchange detection module 34 detects that data is no longer being exchanged therebetween (and/or until the external programmer 40 sends a data cessation signal to the IMD 42). After the data has been exchanged between the IMD 32 and the programmer 40, the power setting adjustment module 36 may cycle the IMD 32 to a low power setting 52a (such as a power level setting that enables communication over the first frequency band, such as the 2.45 GHz band). For example, the programmer 40 may transmit a sleep signal to the IMD 42, indicating that an initial data exchange is complete. The IMD 32 receives the sleep signal and transitions to the low power setting or sleep mode. Once the IMD 32 enters the low power setting or sleep mode, the IMD 32 may activate a re-wakeup timer that re-wakes the IMD 42 at the end of the timer (for example, the end of the timed period set by the re-wakeup timer) so that the IMD 32 transitions back to the high power setting to communicate with the programmer 40. At the same time, the programmer 40 may continue to transmit wakeup request signals or packets over the second frequency band to keep the second frequency band occupied. For example, the programmer 40 may transmit wakeup request signals to the IMD 32 in the same sub-channel within the second frequency band. The sub-channel may be the same as used for data exchange.

The low power setting 52a may be a sleep mode in which the IMD 42 ceases to communicate with the programmer 40, or communicates at a reduced power setting, such as a power level setting that enables communication over the first frequency band, or a power level setting that is 5-10% of the power setting during the data exchange 48. The reduced or low power level setting may be a sufficient power level setting to operate the re-wakeup timer, for example. Alternatively, the reduced power setting may be greater or less than 5-10% of the power consumed during the data exchange 48. The power setting adjustment module 36 may transition the IMD 42 to a full power setting 54a in order to determine if the programmer 40 is attempting to exchange data with the IMD 42. For example, once in the low power setting 52a, the IMD 42 may transition to the full power setting 54a after a predetermined of time, such as 200 milliseconds, which may be predetermined by the re-wakeup timer. Optionally, the low power setting 52a may be shorter or longer than 200 milliseconds.

If the data exchange detection module 34 of the IMD 42 determines at the full power setting 54a that the programmer 40 is not attempting to exchange data with the IMD 42, the power adjustment module 36 of the IMD 42 may switch back to a low power setting 52b, which may be a predetermined period. Optionally, during the full power setting 54a, the external programmer 40 may transmit a data cessation signal that instructs the IMD 42 to return to the low power setting or sleep mode. The full power setting 54a may be a sniffing period used to determine if the programmer 40 is attempting to exchange data with the IMD 42. The full power setting 54a may last for a shorter period of time, such as 25% of the duration of the low power setting 52a, if no communication request from the programmer 40 is detected by the IMD 42. Alternatively, the full power setting 54a may be greater or less than 25% of the duration of the low power setting 52a.

The IMD 42 continues to cycle between low power settings 52a, 52b, 52c, and 52d and full power settings 54a, 54b, 54c, until the IMD 42 detects that the programmer 40 is attempting to exchange data with the IMD 42 or close the communication or data exchange session. For example, the IMD 42 detects a data exchange request and remains in the full power setting 54d until the data is exchanged between the IMD 42 and the programmer 40. After the data is exchanged, the IMD 42 may switch back to a low power setting. If, however, the IMD 42 receives a close link communication 56 from the programmer 40, the IMD 42 switches back to a power level associated with communication over the first frequency band, in which the IMD 42 periodically scans for a wakeup call from the programmer 40.

As described above, the low power settings 52a, 52b, 52c, and 52d may be predetermined set periods of time. Each of the low power settings 52a, 52b, 52c, and 52d may last the same amount of time (although not at the same time). Optionally, the IMD 42 may be configured so that the low power settings 52a, 52b, 52c, and 52d vary depending on whether or not data is exchanged between the IMD 42 and the programmer 40. For example, if the IMD 42 does not exchange data with the programmer 40 after a first low power setting, the second low power setting may be shorter than the first low power setting. If the IMD 42 does not exchange data with the programmer 40 after the second low power setting. the third low power setting may be shorter than the second low power setting. Alternatively, the low power settings may increase in duration if no data is exchanged between the IMD 42 and the programmer 40.

Similarly, the high power settings 54a, 54b, and 54c may be predetermined set periods of time. Each of the high power settings 54a, 54b, and 54c may last the same amount of time (although not at the same time). Optionally, the IMD 42 may be configured so that the high power settings 54a, 54b, and 54c vary depending on whether or not data is exchanged between the IMD 42 and the programmer 40. For example, if the IMD 42 does not exchange data with the programmer 40 after a first high power setting, the second high power setting may be shorter than the first high power setting. If the ND 42 does not exchange data with the programmer 40 after the second high power setting, the third high power setting may be shorter than the second high power setting. Alternatively, the high power settings may increase in duration if no data is exchanged between the IMD 42 and the programmer 40.

Also, alternatively, the duration of one or both of the low and high power settings may be based on a quality of the communication link between the IMD 42 and the programmer 40. It the communication link is robust and strong with little or no attenuation, the duration of the low power settings may be longer, while the duration of the high power settings may be shorter. If, however, the communication link is weaker, the duration of the low power settings may be shortened, while the duration of the high power settings may be lengthened. In short, the chances of the IMD 42 inadvertently missing a data signal increases as the quality of the communication link decreases. Accordingly, the duration of high power settings in which the IMD 42 scans for data requests from the programmer may be longer in order to reduce the chance that the IMD 42 misses a data exchange request.

Figure 3B:
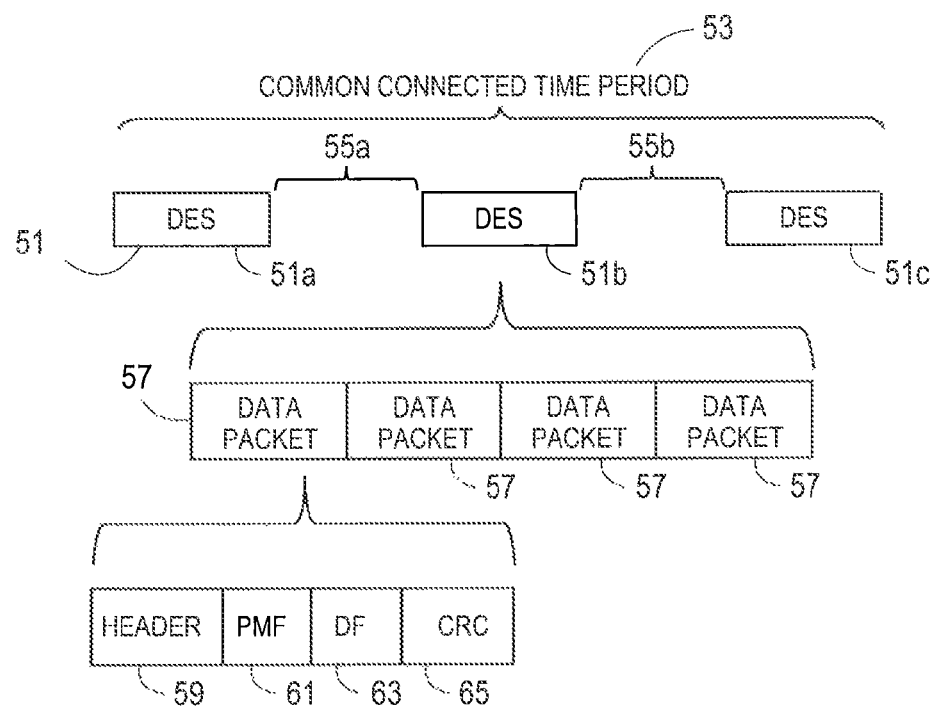
FIG. 3B illustrates a schematic of data exchanged during a data exchange session, according to an embodiment of the present disclosure.

FIG. 3B illustrates a schematic of data exchanged during a data exchange session (DES) 51, according to an embodiment of the present disclosure. As shown, during a common connected time period 53, a plurality of data exchange sessions 51 may be initiated between the programmer 40 and the IMD 42 (shown in FIG. 3A). An initial data exchange session 51a is separated from a subsequent data exchange session 51b by an intra-data exchange session idle period or non-transmission period 55a, while the data exchange session 51b is separated from a subsequent data exchange session 51c by an intra-data exchange session idle period or non-transmission period 55b. During the intra-data exchange session idle periods 55a and 55b, no data is exchanged between the programmer 40 and the IMD 42.

During each data exchange session 51, the IMD 42 operates at the high power setting. The high power setting is a power level setting that allows transmission and/or reception of data packets 57 between the IMD 42 and the programmer 40. During each intra-data exchange session idle period 55a and 55b, the IMD 42 operates at the low power setting. The low power setting is a power level that is less than the high power setting, and allows the IMD 42 to conserve energy during periods when no data is being exchanged between the IMD 42 and the programmer.

Each data packet 57 may include a header 59, a packet management field (PMF) 61, a data field (DF) 63, and a code redundancy check (CRC) 65. The header 59 may include information regarding the source and destination of the data packet 57. The packet management field 61 may include information related to the type, nature, and length of data being transmitted. The data field 63 may include the actual data being transmitted. The CRC 65 is configured to provide a redundancy check with respect to the data packet 57 to ensure that the proper data is being transmitted.

Figure 4:
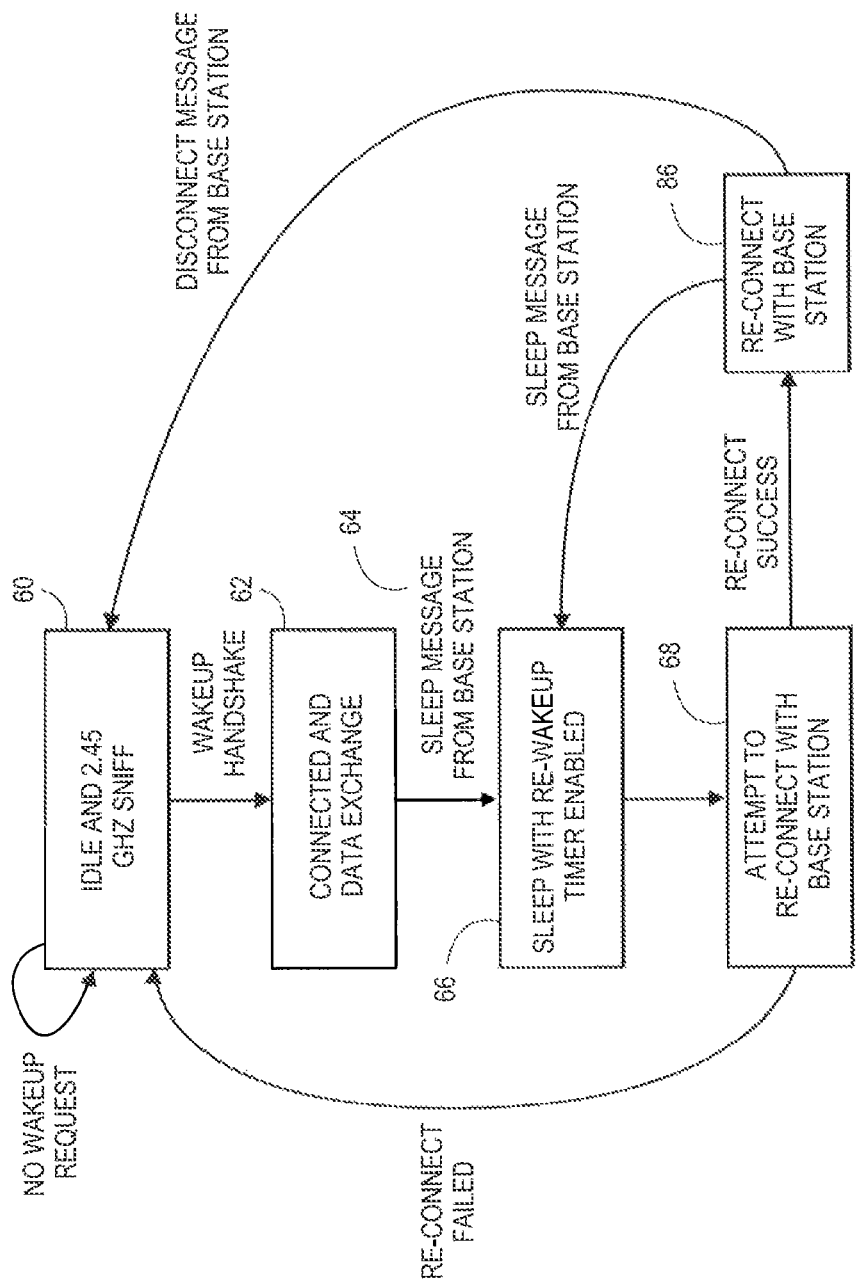
FIG. 4 illustrates a flow chart of a process of operating an IMD, according to an embodiment of the present disclosure.

FIG. 4 illustrates a flow chart of a process of operating an IMD, according to an embodiment of the present disclosure. The method begins at 60, in which an IMD is idle and periodically sniffs or scans at a first frequency band, such as a 2.45 GHz band. If the ND does not detect a wakeup request from a programmer, the method remains at 60.

If, however, the IMD detects a wakeup request or handshake from the programmer, the process continues to 62, in which the IMD switches to a second frequency band, such as the MICS band, and connects and exchanges data with the programmer.

The IMD may detect that the programmer is no longer exchanging data with the IMD. Alternatively, the programmer may send a signal to the IMD that data exchange has stopped. For example, the IMD may receive a sleep message from the programmer or base station at 64. Then, at 66, the IMD may transition to a low power setting or sleep mode with a re-wakeup timer activated. When the re-wakeup timer expires, the IMD attempts to reconnect with the programmer or base station at 68. During the reconnection attempt, the IMD may transition to the high power setting. A successful reconnection reconnects the IMD with the programmer or base station at 70. If the programmer or base station is still in a communication mode, but is not currently requesting a data exchange with the IMD, the process returns to 66. If, however, the communication or data exchange session has expired such that all data is exchanged between the programmer or base station and the IMD, the process returns to 60.

Figure 5:
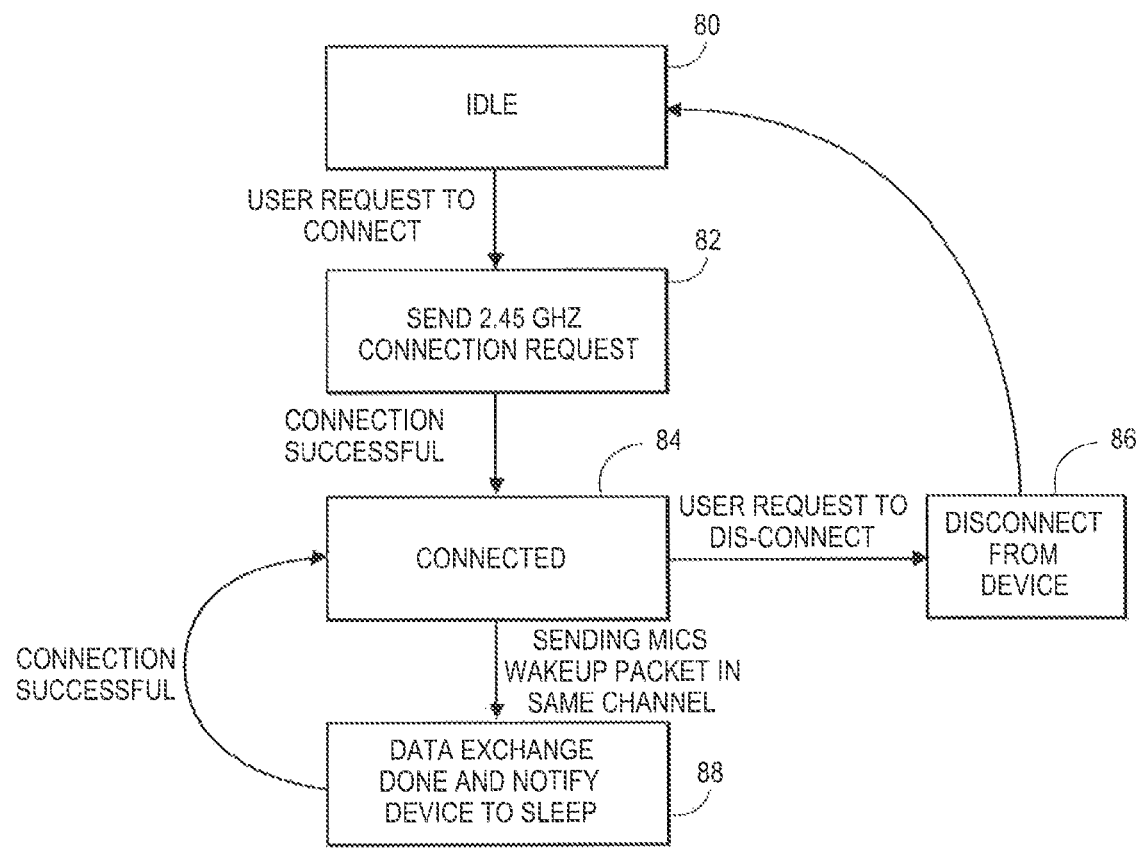
FIG. 5 illustrates a flow chart of a process of operating an external programmer or base station, according to an embodiment of the present disclosure.

FIG. 5 illustrates a flow chart of a process of operating an external programmer or base station, according to an embodiment of the present disclosure. The process begins at 80, in which the base station may be idle. If a user requests a connection between the programmer and the IMD to exchange data, the process continues to 82, in which the base station sends a connection request over a first frequency band, such as the 2.45 GHz band. If the IMD receives the requests and transitions to the second frequency band, such as the MICS band, the process moves to 84, in which the programmer and the base station connect during a communication or data exchange session. If the user requests disconnection, the external programmer disconnects from the IMD at 86, and the process returns to 80. If, however, the IMD and the external programmer remain communicatively connected, data is exchanged and the programmer may notify the IMD to enter a sleep mode after the data has been exchanged. Then, at 88, the programmer may transmit a wakeup request signal, such as an MICS wakeup packet, to the IMD. If the IMD receives the wakeup request signal, such as during a periodic sniff (such as on the second frequency band, for example, the MICS band) at a high power setting, the IMD and the base station reconnect to exchange data, and the process returns to 84.

Figure 6:
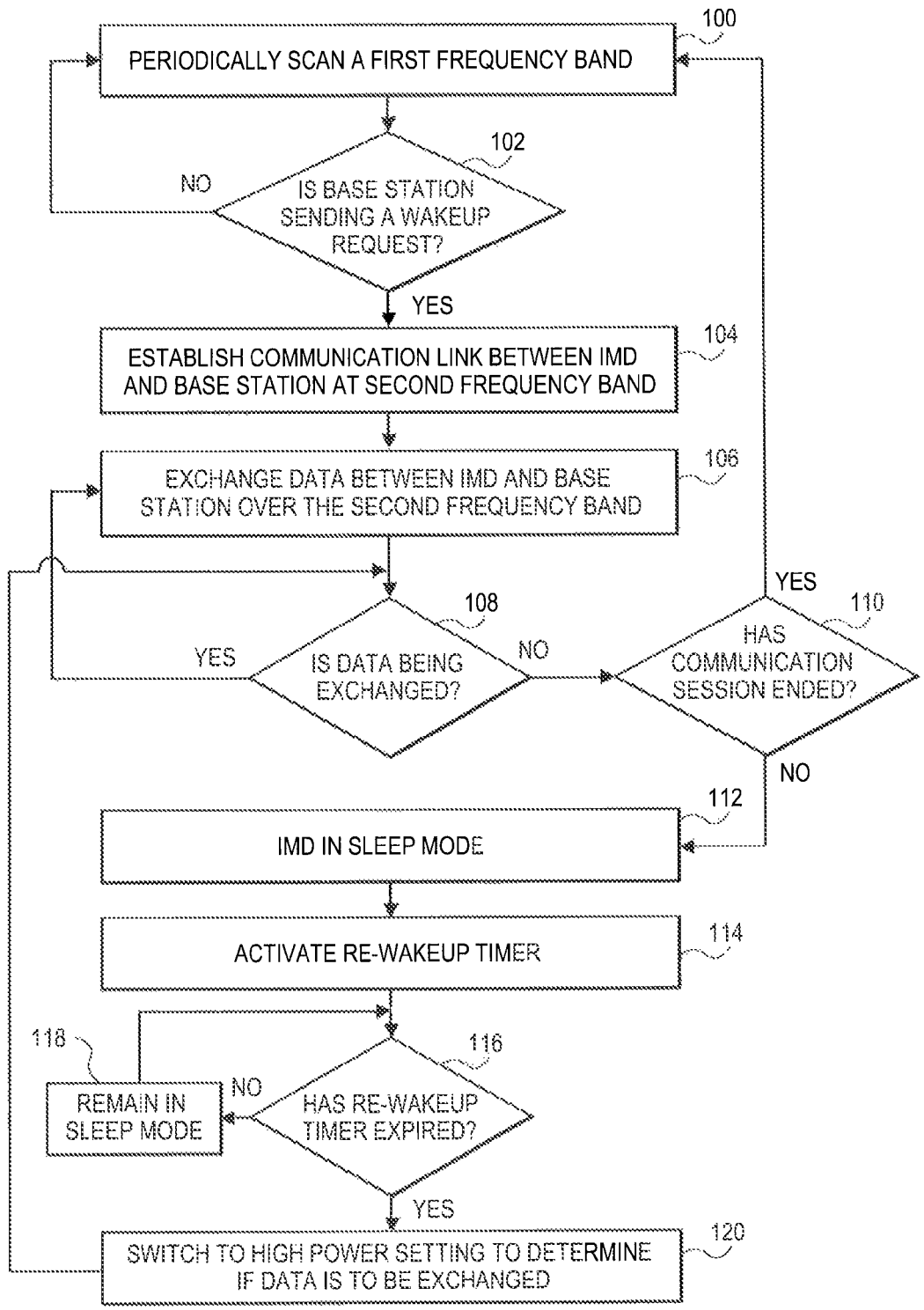
FIG. 6 illustrates a flow chart of a process of an IMD interacting with an external programmer or base station, according to an embodiment of the present disclosure.

FIG. 6 illustrates a flow chart of a process of an IMD interacting with an external programmer or base station, according to an embodiment of the present disclosure. At 100, the IMD periodically scans a first frequency band for a wakeup request signal. For example, the IMD operates at a low power setting to communicate over a low frequency band or channel, such as the 2.45 GHz band. At 102, based on the periodic scanning or sniffing, the IMD determines if a base station is sending a wakeup request or signal. If the IMD does not detect a wakeup request or signal, the process returns to 100.

If, however, the IMD detects a wakeup request or signal on the first frequency band, the process continues to 104, in which a communication or data exchange link is established between the IMD and the base station or external programmer at a channel within the second frequency band or channel, such as the MICS band. When the IMD switches to the second frequency band, the power level setting of the IMD may be increased to accommodate communication on the second frequency band. As such, when communicating over the second frequency band, the IMD may be in a high power level setting.

At 106, a communication or data exchange session during a common connected time period is established and data is exchanged between the IMD and the base station or external programmer over the second frequency band. After initial data (such as a program upload or update) is exchanged, the process continues to 108, in which it is determined whether additional data is being exchanged. For example, a data exchange detection module within the IMD may determine whether data is still being exchanged. Optionally, the base station or external programmer may send a data cessation signal to the IMD, indicating that no more data is currently being exchanged between the IMD and the base station or external programmer. If data is still being exchanged, the process returns to 106.

If, however, data is not being exchanged between the IMD and the base station or external programmer, the process moves to 110, in which it is determined whether the communication or data exchange session has expired. For example, the base station or external programmer may send an end link signal to the IMD indicating that the communication session has expired. If the communication session has expired, the process returns to 100.

If, however, the communication session has not expired (but data is no longer being exchanged between the IMD and the base station), the process continues to 112, in which the IMD transitions to sleep mode or a low power setting. For example, the sleep mode or low power setting may be a power level that enables the IMD to communicate over the first frequency band, such as the 2.45 GHz band. The IMD may automatically transition to the sleep mode or low power setting, such as through a power setting adjustment module. Optionally, the base station or external programmer may instruct the IMD to enter the sleep mode.

As the IMD enters the sleep mode, a re-wakeup timer is activated within the IMD at 114. At 116, it is determined if the re-wakeup timer has expired. If the re-wakeup timer has not expired, the IMD remains in the sleep mode at 118, and the process returns to 116. The duration of the re-wakeup timer may be, for example 200 milliseconds. Alternatively, the duration of the re-wakeup timer may be greater or less than 200 milliseconds.

If, however, the re-wakeup timer has expired, the process continues to 120, in which the IMD switches back to the high power setting, such a power level that enables communication over the second frequency band, to determine if data is to be exchanged with the base station or external programmer. The process then returns to 108.

Thus, embodiments of the present disclosure provide a system and method in which the IMD may enter a low power setting or sleep mode during a communication or data exchange session with an external programmer or base station. The IMD may be programmed to detect when a data exchange is complete and may automatically enter the low power setting or sleep mode. Optionally, the external programmer may send a sleep signal to the IMD that indicates that the data exchange is complete and that the IMD should enter the low power setting or sleep mode. Once the sleep mode or low power setting is initiated, the IMD may activate a timer. After the timer expires, the IMD may re-wake and communicate with the programmer in the same channel of the second frequency band, such as the MICS band, to determine if additional data is to be exchanged. In this manner, the IMD conserves energy. In short, the IMD may be enter the sleep mode or the low power setting, whether automatically or through a command received from the programmer, when there is no data to be exchanged.

Embodiments of the present disclosure provide a system and method of duty-cycle modulation (such as through the transitions between low and high power settings) in order to manage a communication link between an IMD and a programmer or base station. The transition between the high power setting and the low power setting between the IMD and the programmer may be short, such as less than 200 milliseconds, thereby providing an almost seamless link re-establishment.

Figure 7:
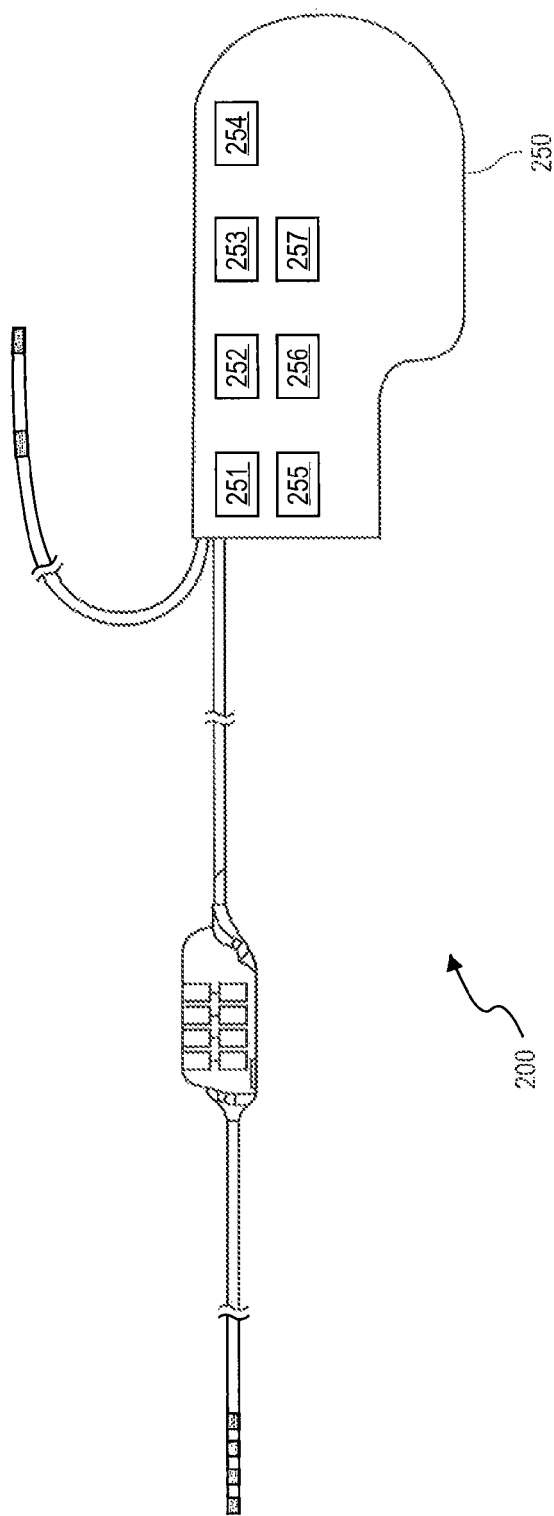
FIG. 7 illustrates a schematic view of a neurostimulation system, according to an embodiment of the present disclosure.

FIG. 7 illustrates a schematic view of a neurostimulation system 200, according to an embodiment of the present disclosure. Neurostimulation systems (NS) include devices that generate electrical pulses and deliver the pulses to nerve tissue to treat a variety of disorders. Spinal cord stimulation (SCS) is the most common type of neurostimulation. In SCS, electrical pulses are delivered to nerve tissue in the spine to control or alleviate chronic pain. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue.

Neurostimulation systems generally include a pulse generator and one or more leads. A stimulation lead includes a lead body of insulated material that encloses wire conductors. The distal end of the stimulation lead includes multiple electrodes that are electrically coupled to the wire conductors. The proximal end of the lead body includes multiple terminals, which are also electrically coupled to the wire conductors that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an extension.

The system 200 is configured to generate electrical pulses for application to nerve tissue of a patient. For example, the system 200 may be adapted to stimulate spinal cord tissue, peripheral nerve tissue, deep brain tissue, cortical tissue, or any other nervous tissue within a patient's body.

The system 200 includes an external or implantable NS device 250 that is configured to generate electrical pulses for application to a nerve system of a patient. The implantable NS device 250 is an example of an IMD that may communicate with an external programmer or base station, as described above.

The implantable NS device 250 may include a metallic housing that encloses controller 251, pulse generating circuitry 252, battery 253, recharging circuit 254, far-field and/or near field communication circuitry 255, battery charging circuitry 256, switching circuitry 257, and the like. The controller 251 may include a microcontroller or other suitable processor for controlling the various other components of the device. Additionally, the controller 251 may include the power regulator 28, shown and described with respect to FIG. 2. Software code is stored in memory of the NS device 250 for execution by the microcontroller or processor to control the various components of the device.

Alternatively, the systems and methods described in the present application may be used with various other IMDs other than neurostimulation devices. For example, the systems and methods described in the present application may be used with implantable cardiac pacemakers.

Figure 8:
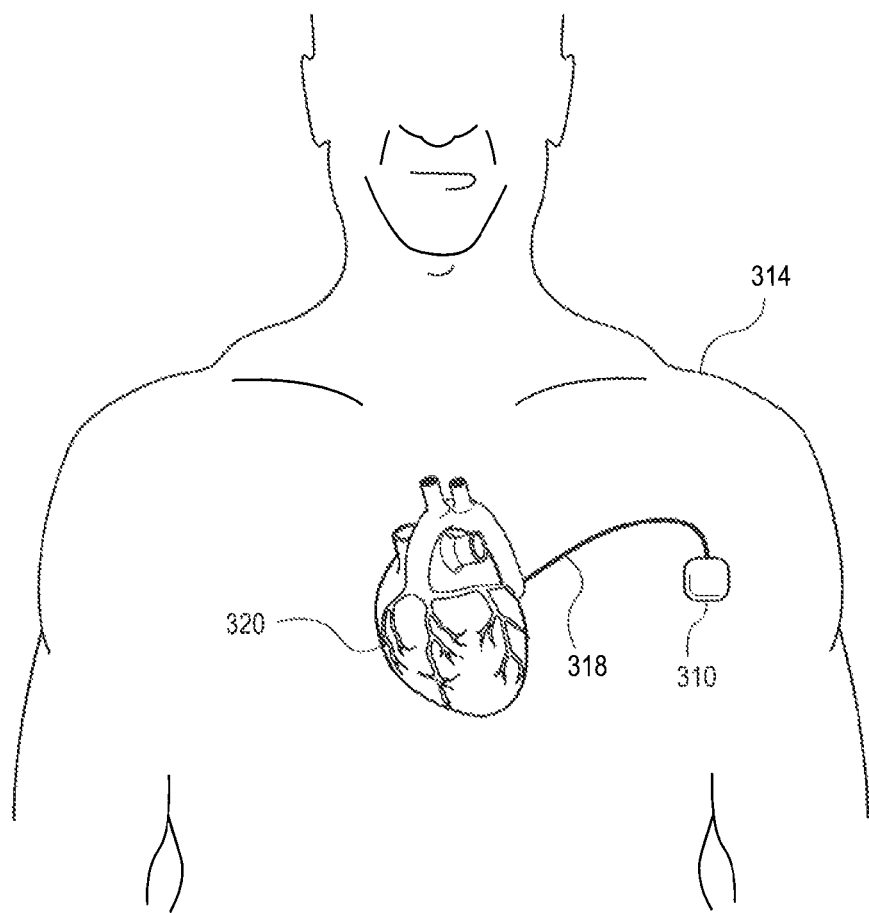
FIG. 8 illustrates an IMD implanted in a patient, according to an embodiment of the present disclosure.

FIG. 8 illustrates an IMD 310 implanted in a patient 314, according to an embodiment of the present disclosure. The IMD 310 is an example of an IMD that may communicate with an external programmer or base station, as described above. The IMD 310 may be an implantable pacemaker, for example. One or more leads 318 provide a patient connection interface that connects the IMD 310 to the heart 320, for example. The IMD 310 may provide therapy, such as stimulation of the heart 320 and rhythm control, through the lead(s) 318. In order to transmit and receive RF signals, the IMD 310 may include a transceiver and/or an antenna.

Figure 9:
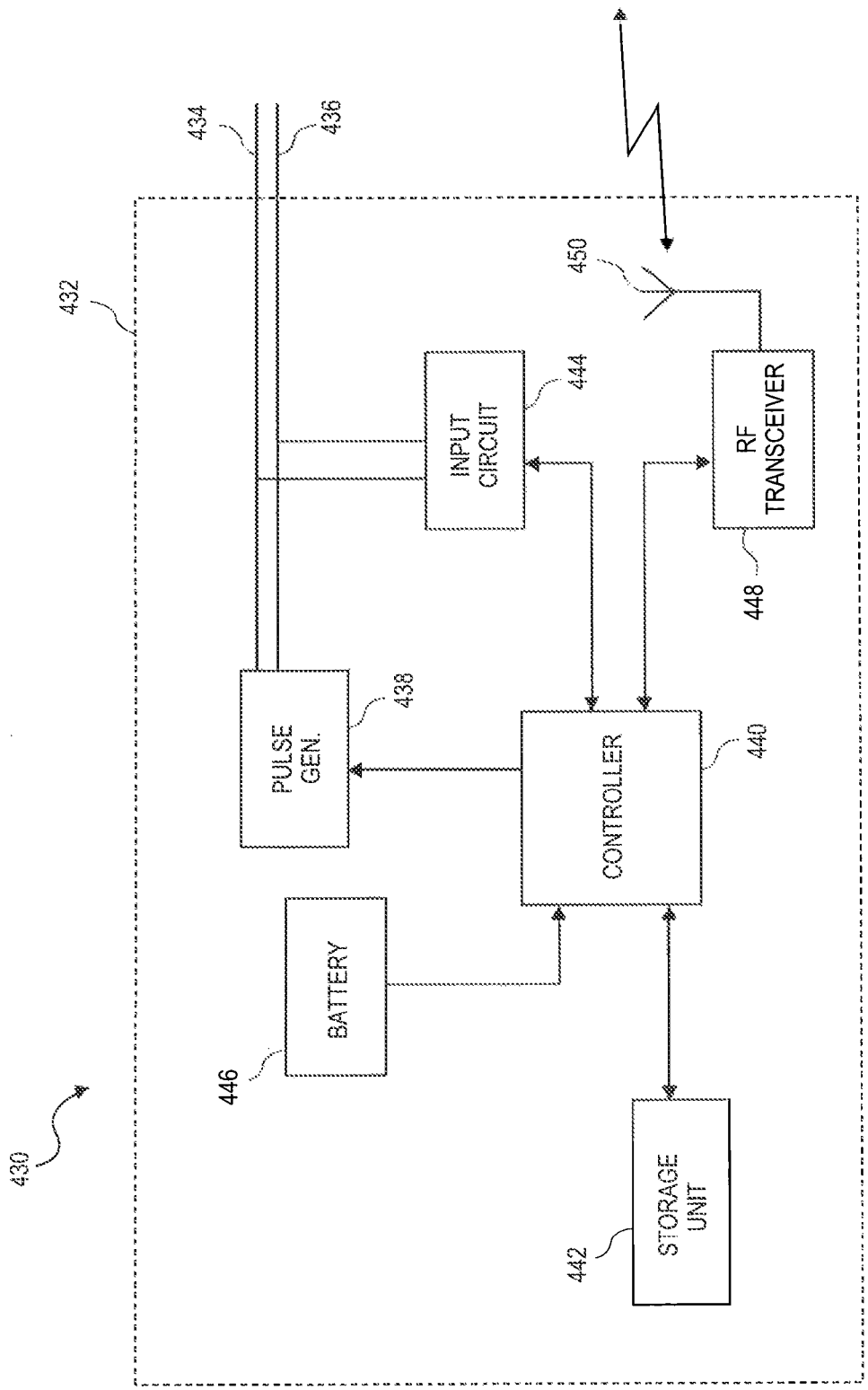
FIG. 9 illustrates a functional block diagram of an IMD, according to an embodiment of the present disclosure.

FIG. 9 illustrates a functional block diagram of an IMD 430, according to an embodiment of the present disclosure. The IMD 430 is an example of an IMD that may communicate with an external programmer or base station, as described above. The IMD 430 may be a bi-ventricular pacemaker, for example. The IMD 430 may include a housing 432 that is hermetically sealed and biologically inert. The housing 432 may be conductive and may thus serve as an electrode. The IMD 430 may be connectable to one or more leads, such as a ventricular lead 434 that is configured to be implanted in a right ventricle of the heart and an atrial lead 436 that is configured to be implanted in a right atrium of the heart. The leads 434 and 436 may include one or more electrodes, such as a tip electrode or a ring electrode that may be configured to measure impedance or transmit pacing pulses for causing depolarization of cardiac tissue adjacent to the electrodes generated by a pace pulse generator 438 under influence of a controller or controlling circuit 440 that may include a microprocessor. The controller 440 is configured to control parameters, such as pace pulse parameters. The pace pulse parameters may include output voltage and pulse duration, for example.

A memory or storage unit 442 may be connected to the controller 440. The storage unit 442 may include a random access memory (RAM), a non-volatile memory, such as a read-only memory (ROM), a scratchpad, and the like. Detected signals from the patient's heart may be processed in an input circuit 444 and forwarded to the controller 440 for use in logic timing determination. The IMD 430 may be powered by a battery 446, which supplies electrical power to all active electrical components of the pacemaker.

The IMD 430 may include an RF module or transceiver 448 for wireless communication of signals to/from an external programmer, such as any of the programmers or base stations described above. Medical personnel may prefer to monitor and/or adjust parameters of the IMD 430 or to perform reprogramming. The transceiver 448 may be connected to one or more antennas 450 at different times.

The RF module or transceiver 448 may be operatively connected to the antenna(s) 450 and configured to periodically listen for an RF communication or wakeup request. As an example, the RE transceiver 448 may periodically, such as every two seconds, listen for an RF communication request over the first frequency band, such as the 2.45 GHz band. If the RF transceiver 448 detects a communication request from an external programmer, the RF transceiver 448 sends a signal to the controller 440, which then switches the RF transceiver 448 from the first frequency band to the second frequency band, such as the MICS band, in order to communicate with the external programmer. Before or after the RF transceiver 448 switches to the second frequency band, the controller 440, through the RF transceiver 448, transmits a response signal to the external programmer, which receives the response signal and acknowledges that the IMD 430 is communicating with the external programmer. As such, the external programmer may wake the IMD 430 up through a communication request or signal over the first frequency band. The external programmer may wake the IMD 430 up when positioned in close proximity with the IMD 430. Optionally, a separate and distinct wand may be placed in close proximity with the IMD 430 in order to wake the IMD 430 up so that a communication link may be established between the IMD 430 and the external programmer.

Figure 10:
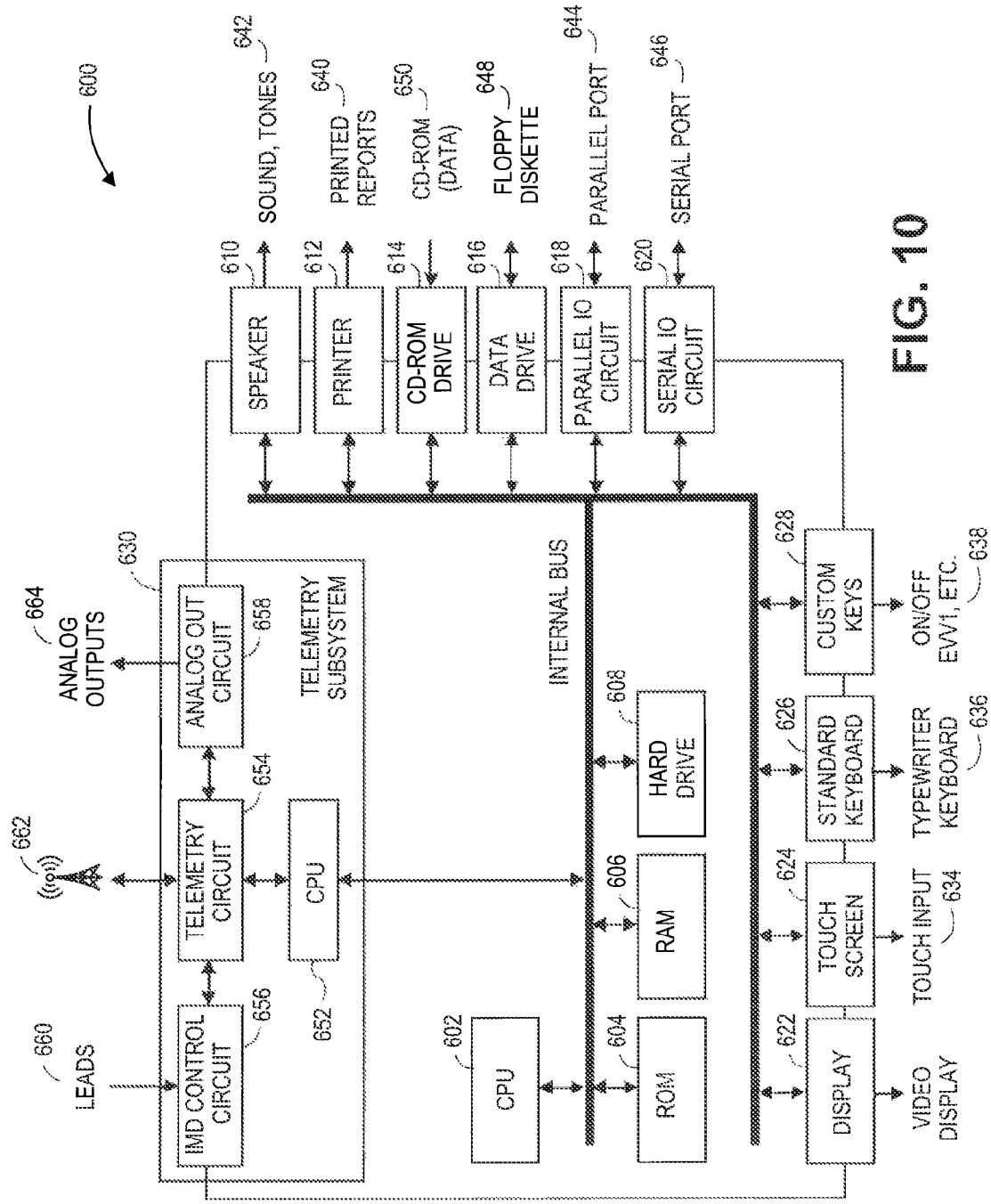
FIG. 10 illustrates a functional block diagram of an external programmer or base station, according to an embodiment of the present disclosure.

FIG. 10 illustrates a functional block diagram of an external device 600, such as an external programmer or base station, according to an embodiment of the present disclosure. The external device 600 may be configured to interface with IMDs, as described above. Various other external devices may be used in place of the external device 600. The external device 600 is for illustration purposes only, and it is understood that the circuitry could be duplicated, eliminated or disabled in any desired combination.

The external device 600 may be or include a workstation, a portable computer, an IMD programmer, a tablet, PDA, a cell phone and/or the like. The external device 600 includes an internal bus that connects/interfaces with a Central Processing Unit (CPU) 602, ROM 604, RAM 606, a hard drive 608, a speaker 610, a printer 612, a CD-ROM drive 614, a floppy drive 616, a parallel I/O circuit 618, a serial I/O circuit 620, a display 622, a touch screen 624, a standard keyboard connection 626, custom keys 628, and a telemetry subsystem 630. The internal bus is an address/data bus that transfers information between the various components described herein. The hard drive 608 may store operational programs as well as data, such as waveform templates and detection thresholds.

The CPU 602 may include a microprocessor, a microcontroller, or equivalent control circuitry, designed specifically to control interfacing with the external device 600 and with the IMD. The CPU 602 may include RAM or ROM memory, logic and timing circuitry, state machine circuitry, and I/O circuitry to interface with the IMD. The touch screen 624 may display graphic information relating to the IMD. The display 622 may display information related to the processes described herein. The touch screen 624 accepts a user's touch input 634 when selections are made. The keyboard 626 (e.g., a typewriter keyboard 636) allows the user to enter data to the displayed fields, as well as interface with the telemetry subsystem 630. Furthermore, custom keys 628 turn on/off 638 the external device 600. The printer 612 prints copies of reports 640 for a physician to review or to be placed in a patient file, and speaker 610 provides an audible warning (e.g., sounds and tones 642) to the user. The parallel I/O circuit 618 interfaces with a parallel port 644. The serial I/O circuit 620 interfaces with a serial port 646. The floppy drive 616 accepts diskettes 648. Optionally, the floppy drive 616 may include a USB port or other interface capable of communicating with a USB device such as a memory stick. The CD-ROM drive 614 accepts CD ROMs 650.

The telemetry subsystem 630 may include a central processing unit (CPU) 652 in electrical communication with a telemetry circuit 654, which communicates with both an IMD control circuit 656 and an analog out circuit 658. The circuit 656 may be connected to leads 660. Optionally, the external device 600 may communicate wirelessly with the IMD.

The telemetry circuit 654 may be connected to a transceiver 662. The analog out circuit 658 includes communication circuits to communicate with analog outputs 664. The external device 600 may wirelessly communicate with the IMD utilizing various protocols, such as Bluetooth, GSM, infrared wireless LANs, HIPERLAN, 3G, satellite, as well as other packet-based data protocols, and the like. Alternatively, a hard-wired connection may be used to connect the external device 600 to the IMD.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor may also include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer" or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" may be interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method for operating an implantable medical device (IMD) implanted within a patient, the method comprising:
    scanning by the IMD for a wakeup request signal from an external programmer over a first frequency band at a first power level;
    switching to communication over a second frequency band at a second power level after the IMD detects the wakeup request signal, wherein the second power level exceeds the first power level and wherein the switching operation initiates an initial data exchange session during a common connected time period between the IMD and the external programmer; and
    cycling between the first and second power levels during the common connected time period based on whether data is being exchanged between the external programmer and the IMD, wherein, while in the first power level of the common connected time period, the IMD selectively communicates with the external programmer over the first frequency band at the first power level including selective transmission of signals from the IMD to the external programmer over the first frequency band at the first power level and wherein, while in the second power level of the common connected time period, the IMD selectively communicates with the external programmer over the second frequency band at the second power level.

2. The method of claim 1, wherein the cycling operation comprises:
    operating at the first power level during the common connected time period when no data is being exchanged between the external programmer and the IMD and when communicating over the first frequency band, and
    operating at the second power level during the initial data exchange session or one or more subsequent data exchange sessions within the common connected time period when data is being exchanged between the external programmer and the IMD and when otherwise communicating over the second frequency band.

3. The method of claim 1, further comprising:
    determining that no data is being exchanged during the common connected time period;
    switching to the first power level during the common connected time period after the determining operation;
    activating a re-wakeup timer after the determining operation during the common connected time period; and
    switching to the second power level at the end of the re-wakeup timer to determine whether the external programmer is attempting to exchange data with the IMD.

4. The method of claim 1, wherein the cycling operation comprises communicating with the external programmer at the second frequency band at the second power level during the initial data exchange session or one or more subsequent data exchange sessions within the common connected time period.

5. The method of claim 1, wherein the first frequency band includes a 2.45 GHz band, and wherein the second frequency band includes a Medical Implant Communication Service (MICS) band.

6. The method of claim 1, further comprising:
    receiving a data cessation signal from the external programmer; and
    switching back to the scanning operation upon the receiving operation.

7. The method of claim 1, wherein the IMD comprises a neurostimulator.

8. The method of claim 1, wherein the initial data exchange session includes one or more data packets, wherein the one or more data packets comprises a header, a packet management field, a data field, and a code redundancy check.

9. A system for conserving power during a common connected time period, the system comprising:
    an external programmer configured to transmit a wakeup request signal; and
    an implantable medical device (IMD) configured to be implanted within a patient and communicate with the external programmer, wherein the IMD is configured to scan for the wakeup request signal transmitted by the external programmer over a first frequency band at a first power level, and switch to a second frequency band at a second power level after the IMD detects the wakeup request signal to initiate an initial data exchange session during the common connected time period, wherein the second power level exceeds the first power level and wherein the IMD is configured to cycle between the first and second power levels during the common connected time period based on whether data is being exchanged between the external programmer and the IMD, and wherein, while in the first power level of the common connected time period, the IMD selectively communicates with the external programmer over the first frequency band at the first power level including selective transmission of signals from the IMD to the external programmer over the first frequency band at the first power level and wherein, while in the second power level of the common connected time period, the IMD selectively communicates with the external programmer over the second frequency band at the second power level.

10. The system of claim 9, wherein the IMD is configured to operate at the first power level during the common connected time period when no data is being exchanged between the external programmer and the IMD and when communicating over the first frequency band, and wherein the IMD is configured to operate at the second power level during the initial data exchange session or one or more subsequent data exchange sessions within the common connected period when data is being exchanged between the external programmer and the IMD and when otherwise communicating over the second frequency band.

11. The system of claim 9, wherein the IMD comprises a re-wakeup timer that is configured to be activated after one or both of the external programmer and the IMD determine that no data is being exchanged during the common connected time period, wherein the IMD is configured to switch to the second power level at the end of the re-wakeup timer to determine whether the external programmer is attempting to exchange data with the IMD.

12. The system of claim 9, wherein the IMD is configured to communicate with the external programmer at the second frequency band at the second power level during the initial data exchange session or one or more subsequent data exchange sessions within the common connected time period.

13. The system of claim 9, wherein the first frequency band includes a 2.45 GHz band, and wherein the second frequency band includes a Medical Implant Communication Service (MICS) band.

14. The system of claim 9, wherein the IMD comprises a wakeup detection module configured to scan for the wakeup request signal from the external programmer over the first frequency band at the first power level.

15. The system of claim 9, wherein one or both of the external programmer and the IMD comprises a data exchange detection module configured to detect whether data is being exchanged between the external programmer and the IMD.

16. The system of claim 9, wherein one or both of the external programmer and the IMD comprises a power setting adjustment module configured to cycle the IMD between the first and second power levels during the common connected time period based on whether data is being exchanged between the external programmer and the IMD.

17. The system of claim 9, wherein, after receiving a data cessation signal from the external programmer, the IMD is configured to switch back to scanning for the wakeup request signal from the external programmer over the first frequency band at the first power level.

18. The system of claim 9, wherein the IMD comprises a neurostimulator.

19. The method of claim 1, wherein a duration within which the IMD operates at a particular power level is selectively adjusted based on a quality of a communication link between the IMD and the external programmer.

20. The method of claim 19, wherein, if the quality of the communication link increases, a duration within which the IMD operates at the first power level is increased relative to a duration within which the IMD operates at the second power level.

21. The system of claim 1, wherein a duration within which the IMD operates at a particular power level is selectively adjusted based on a quality of a communication link between the IMD and the external programmer.

22. The system of claim 21, wherein, if the quality of the communication link increases, a duration within which the IMD operates at the first power level is increased relative to a duration within which the IMD operates at the second power level.

* * * * *